(12) United States Patent
Foh et al.

(10) Patent No.: US 11,590,261 B2
(45) Date of Patent: *Feb. 28, 2023

(54) METHOD FOR THE PREPARATION OF BIOLOGICAL TISSUE FOR DRY USE IN AN IMPLANT

(71) Applicant: BIOTRONIK AG, Buelach (CH)

(72) Inventors: Nina Foh, Fuerth (DE); Alexander Rzany, Nuremberg (DE); Wilhelm Erdbruegger, Dortmund (DE)

(73) Assignee: Biotronik AG, Bülach (CH)

( * ) Notice: Subject to any disclaimer, the term of this patent is extended or adjusted under 35 U.S.C. 154(b) by 507 days.

This patent is subject to a terminal disclaimer.

(21) Appl. No.: 16/551,456

(22) Filed: Aug. 26, 2019

(65) Prior Publication Data

US 2019/0374680 A1  Dec. 12, 2019

Related U.S. Application Data

(63) Continuation-in-part of application No. 14/671,112, filed on Mar. 27, 2015, now Pat. No. 10,390,946.

(30) Foreign Application Priority Data

Apr. 2, 2014  (EP) .................................... 14163120

(51) Int. Cl.
  *A61L 27/36*  (2006.01)
  *A61L 27/58*  (2006.01)
(52) U.S. Cl.
  CPC ......... *A61L 27/3687* (2013.01); *A61L 27/367* (2013.01); *A61L 27/3625* (2013.01); *A61L 27/58* (2013.01); *A61L 2400/18* (2013.01); *A61L 2430/20* (2013.01)
(58) Field of Classification Search
  None
  See application file for complete search history.

(56) References Cited

U.S. PATENT DOCUMENTS

| 4,357,274 A | 11/1982 | Heinz-Helmut |
| 8,105,375 B2 | 1/2012 | Navia et al. |
| 2009/0324684 A1 | 12/2009 | Atanasoska et al. |
| 2010/0030340 A1 | 2/2010 | Wolfinbarger |
| 2012/0143227 A1 | 6/2012 | Steckel et al. |
| 2013/0158658 A1 | 6/2013 | Hayzlett |

(Continued)

FOREIGN PATENT DOCUMENTS

| EP | 2668966 A1 | 12/2013 |
| EP | 2893905 A1 | 7/2015 |

(Continued)

OTHER PUBLICATIONS

Park et al., Korean J. Thorac. Cardiovasc. Surg. 41(1): 12-24 (2008).*
EP1416120.0 European Search Report mailed 28, 2014.

*Primary Examiner* — Erin M. Bowers
(74) *Attorney, Agent, or Firm* — Wagenknecht IP Law Group PC

(57) ABSTRACT

A method of preparing biological tissue for use as a component of an implant, in particular as part of a vascular implant, more particularly as part of a heart valve prosthesis, which can be implanted by a catheter. The biological tissue is decellularized using a detergent, which includes surfactin and deoxycholic acid (DCA).

25 Claims, 11 Drawing Sheets

(56) References Cited

U.S. PATENT DOCUMENTS

2015/0282930 A1\* 10/2015 Lehenberger ....... A61L 27/3625
    623/2.11
2016/0303289 A1\* 10/2016 Rzany ................. A61L 27/3625
2017/0119928 A1    5/2017 Rzany et al.

FOREIGN PATENT DOCUMENTS

| EP | 2926840 | | 10/2015 |
| WO | 1999/066967 A1 | | 12/1999 |
| WO | 2004/052417 A1 | | 6/2004 |
| WO | WO 2004/052417 | \* | 6/2004 |
| WO | 2005/024099 A1 | | 3/2005 |

\* cited by examiner

| Sample | Free Proteins (μg/mg) | Standard Deviation (μg/mg) | % vs. native |
|---|---|---|---|
| Surfactin 0.06%, 12h | 15.85 | 4.03 | 46.36 |
| Surfactin 0.06%, 24h | 14.81 | 1.52 | 43.31 |
| Surfactin 0.06%, 36h | 17.52 | 5.4 | 51.23 |
| Surfactin 0.06%+DCA 1%, 12h | 16.11 | 0.93 | 47.10 |
| Surfactin 0.06%+DCA 1%, 24h | 6.52 | 0.53 | 19.09 |
| Surfactin 0.06%+DCA 1%, 36h | 5.62 | 0.54 | 16.43 |

Fig. 3

| Sample | Residual DNA (ng/mg) | Standard Deviation (ng/mg) | % vs. native |
|---|---|---|---|
| Porcine Pericardium native | 3257.46 | 946.21 | 100.00 |
| DCA 0.5% | 44.79 | 31.15 | 1.37 |
| DCA 1% | 37.23 | 17.09 | 1.14 |
| Surfactin 0.06%+DCA 0.5% | 7.18 | 2.65 | 0.22 |

Fig. 6

| Solution | Saturation Time (min) | Sample size |
|---|---|---|
| Glycerol – 30% | 10.65±2.31 | 9 |
| Glycerol – 100% | 50.75±19.51 | 4 |
| PEG200 – 40% | 11.88±5.69 | 8 |
| PEG200 – 100% | 24.03±1.66 | 3 |
| PEG400 – 40% | 7.69±1.45 | 9 |
| PEG400 – 100% | 26.47±13.14 | 4 |

Fig. 10

METHOD FOR THE PREPARATION OF BIOLOGICAL TISSUE FOR DRY USE IN AN IMPLANT

CROSS REFERENCE TO RELATED APPLICATIONS

This application is a continuation in part of U.S. patent application Ser. No. 14/671,112, filed Mar. 27, 2015, also known as U.S. Pat. No. 10,390,946, which claims benefit of priority to European patent application no. EP 14163120.0 filed Apr. 2, 2014; the content of each is herein incorporated by reference in its entirety.

TECHNICAL FIELD

The present invention relates to a method for the preparation of biological tissue for use as a component of an implant, in particular for use as a component of a heart valve prosthesis, and to an implant, which contains a thusly prepared biological tissue; e.g., in a dried state.

BACKGROUND OF THE INVENTION

The invention is described in the following primarily with reference to methods for preparing tissue for use for an artificial heart valve. Although the present invention is particularly suitable for preparing this type of tissue, it is not limited to this application. The present invention can also be used to prepare blood vessels, skin tissue, ligaments, and the like.

There are basically two different types of heart valve prostheses: mechanical valves, which are artificially produced, usually being made of graphite coated with pyrolytic carbon; and biological prostheses, which are often made of pericardial tissue, which is usually obtained from animal sources (e.g. swine or cattle). The heart valve formed of biological tissue is usually mounted in a base body (e.g. a rigid plastic framework, a self-expanding stent or a balloon-expandable stent), which is then implanted at the position of the natural valve. The present invention describes a method for preparing such tissue for use in a heart valve prosthesis, which performs the function of a natural heart valve.

The tissue of origin must be thoroughly cleaned and prepared before implantation. In so doing, the tissue is modified, to the greatest extent possible, such that the tissue is not recognized by the body as foreign tissue, is not calcified, and has the longest life span possible. Such a method for the preparation of tissue substantially comprises a plurality of steps.

One possible preparation step is the so-called decellularization of the tissue. In this step, cell membranes, intracellular proteins, cell nuclei, DNA (e.g. from cell nuclei and/or mitochondria) and other cellular components are removed as completely as possible from the tissue in order to obtain the purest extracellular matrix possible. Any cells and cellular components remaining in the tissue could potentially cause an unwanted calcification of the biological implant material. The decellularization should be performed in a manner that is so gentle that the structure of the extracellular matrix and the collagen fibers in the extracellular matrix remain as unaffected as possible while ensuring that all cells and cell components contained therein are removed from the tissue.

Another possible preparation step is that of cross-linking the extracellular matrix, in particular the collagen fibers, of the tissue. After decellularization, preferably all cellular components have been removed from the tissue and the biological material consists of only the extracellular matrix. In the case of pericardial tissue, the extracellular matrix is formed primarily of collagen fibers. In order to obtain biological material having the most optimal mechanical properties possible and to prevent rejection reactions by the receiving body, the collagen fibers are cross-linked by means of a suitable cross-linking agent via the incorporation of chemical bonds. Typically, the cross-linking agent binds to free amino groups of the collagen fibers and forms chemically stable compounds between the collagen fibers. This is predominantly the case when glutaraldehyde is used. However, other cross-links are also possible dependent on the applied cross-linking agent. A biological material having long-term stability is thereby obtained from the three-dimensionally arranged collagen fibers, wherein this biological material is no longer recognized as foreign biological material. The stability and strainability of the tissue is markedly increased by means of the three-dimensional cross-linking or linking of the individual collagen fibers via the cross-linking agent. This is decisive, in particular, in the case of use as tissue of a heart valve, where the tissue is intended to open and close, in brief intervals, as a valve. The thusly treated tissue is secured to a support body, usually via suturing. The support body or the support frame can be implanted using surgical techniques. As an alternative, the support frame is self-expanding or can be expanded by means of a balloon such that the heart valve prosthesis can be guided, in the compressed state, to the site of implantation by means of a catheter and can be implanted inside a natural valve or even inside a previously implanted valve (so-called valve-in-valve procedure).

According to the prior art, such heart valve prostheses, which can be implanted by means of a catheter, are stored in a storage solution, i.e., in the moist state. The storage solution is used for the sterile stabilization of the biological tissue. For implantation, the heart valve prosthesis must then be removed from the storage solution in the surgical suite and, after a plurality of rinsing processes, must be mounted on the catheter. This assembly of the heart valve prosthesis in the surgical suite itself is complex and requires a great deal of work. In addition, whether or not the assembly is carried out correctly depends on the skills of the particular surgical team.

Approaches are therefore known in the prior art for drying such biological tissue, and for processing and sterilizing said biological tissue in the dried state. This would make it possible to sterilize, sterile-package, and pre-assemble a total system comprising a catheter and a pre-assembled heart valve prosthesis.

A method for the preparation of a heart valve prosthesis, which includes the processing of dried, biological material, is disclosed in U.S. Pat. No. 8,105,375. According to the method disclosed therein, the biological tissue is fixed or cross-linked with an aldehyde-containing solution (e.g., glutaraldehyde or formaldehyde solution) and, before drying, is treated with at least one aqueous solution, which contains at least one biocompatible and non-volatile stabilizer. The stabilizers that are disclosed are hydrophilic hydrocarbons comprising a plurality of hydroxyl groups and, as examples, water-soluble sugar alcohols such as glycerol, ethylene glycol or polyethylene glycol are mentioned.

SUMMARY OF THE INVENTION

The problem addressed by the present invention is that of designing a method for the preparation of biological tissue, grafts or substrates for use in medical treatments. In some embodiments, the tissue, graft or substrate is prepared for use in an implant (e.g. for dry use thereof or for biological tissue that is not dried in a next step), or as an implant itself. In some embodiments, the methods are used to prepare a coronary bypass graft. In other embodiments, the methods are used to prepare tissue for a heart valve replacement. In other embodiments, the methods are used to prepare tissue, grafts or substrates for use in a wound treatment procedure, such as to treat lacerations or burns. In some embodiments, the methods are used to treat a hernia. In some embodiments, the methods are used to prepare tissue, grafts or substrates for endogenous tissue regeneration, which uses a patient's own body to naturally restore tissue over a biodegradable scaffolding.

Among the advances described herein are methods that provide improved decellularization of biological tissue, grafts or substrates using a specific combination of decellularizing agents, which when used together, gently and effectively remove undesired protein and DNA. The above is achieved in one aspect of the invention by a method of preparing biological tissue, such as for use as a component of a heart valve prosthesis, the method including decellularizing biological tissue with a detergent containing surfactin and deoxycholic acid (DCA).

Surprisingly, it has been found that the combination of surfactin and DCA for decellularization has a significant advantage over the use of surfactin or DCA alone. In particular, when decellularizing only with surfactin, more soluble proteins remain in the tissue than with a combination with DCA. When decellularizing only with DCA, more residual DNA remains in the tissue than in combination with surfactin. It has been surprisingly found that decellularization of biological tissue with a combination of surfactin and DCA permits particularly thorough removal of all these undesired remaining tissue components. Experimentally, it is shown that the combination of surfactin and DCA produces a particularly good decellularizing agent which is better at removing unwanted tissue components than either agent alone.

In one embodiment of the present invention, additionally, alpha-galactosidase epitopes can be removed from the tissue in a further treatment step which may be performed after or before decellularization. Any suitable alpha-galactosidase may be applied for such additional treatment step; e.g., alpha-galactosidase derived from green coffee bean (GCB) or *Cucumis melo*.

The upper limit of the concentration of surfactin results from the solubility of surfactin itself. That is, surfactin is only soluble in relatively small amounts. In other words, too much surfactin results in it being no longer soluble, which is to be avoided. On the other hand, too little surfactin results in a too little effect. Surfactin should be at a concentration that is less than 3%, preferably less than 1%. In preferred embodiments, the decellularizing agent combination contains less than 0.1% surfactin, such as 0.01% to 0.09%. Most preferably, surfactin is provided at 0.06% or about 0.06%.

The upper limit of the concentration of DCA results from the acidic properties of DCA. If too much DCA is used, the solution becomes too acidic. If too little DCA is used, the effect is too weak/weaker than desired. In preferred embodiments, the decellularizing agent contains about 0.1% to 5% DCA, preferably about 0.1% to 3% DCA, more preferably about 0.1% to 2% DCA, even more preferably about 1% or less DCA. Still more preferably, the decellularizing agent contains about 0.5% DCA or 1% DCA. Most preferably, the decellularizing agent contains 0.5% DCA or about 0.5% DCA.

In some embodiments, the decellularized tissue, graft or substrate is cross-linked with a cross-linking agent before assembly, such as into an implant, graft or attached to an implant or graft. Cross-linking the decellularized biological tissue is preferably realized by exposure to a cross-linking agent. Exemplary solutions suitable for cross-linking decellularized tissue include an aldehyde-containing solution, such as a glutaraldehyde-containing solution or a formaldehyde-containing solution. Typically, glutaraldehyde is preferred.

In some embodiments of the present invention, the disclosed decellularization method is applied to tissue or a substrate which is not cross-linked after decellularization. Such a tissue or substrate could be used in instances where cellular ingrowth is preferred, such as when treating a wound or burn with a porous matrix or when used as a means for sealing an implant or graft.

After decellularization and optionally after cross-linking decellularized tissue, the tissue can be subjected to a dimensional and structural stabilization step. It has also been found that exposing the tissue to certain stabilizing agents can significantly improve stabilization of tissue. In a preferred stabilization step, the tissue is exposed to at least one solution, which contains polyethylene glycol, and is exposed to a solution, which contains glycerol, wherein the tissue is exposed either to the two solutions one after the other in any order as first and second solutions, or is exposed to both solutions simultaneously, as a solution mixture. When drying tissue, such as for storage or transportation of the tissue, the stabilization procedure is preferably performed before drying. As a non-limiting example, after decellularization, the stabilization procedure can be performed by immersing tissue in a series of one or more stabilizing solutions of glycerol and polyethylene glycol as described herein to sufficiently saturate the tissue with stabilizing agents to ultimately produce a stable, dry tissue. Saturation times can vary but typically take about 5 minutes to 2 hours or 5 minutes to 15 minutes depending on characteristics of the tissue. The stabilized tissue may be dried by housing the tissue in a climate chamber and reducing relative humidity, typically from 95% to 10% over 12 hours at 37° C.

Targeted protection of the structure of the biological tissue is obtained by means of the targeted selection and combination of polyethylene glycol and glycerol. By means of the targeted combination of polyethylene glycol and glycerol, a macroscopic dimensional stability of the treated biological tissue during drying is achieved, as in the prior art, but also the microscopic tissue structures are protected and maintained by means of the stabilization of the hydrogen bridges. In addition, specific protection of the biological tissue to be dried is obtained by means of the combination. Glycerol and low molecular weight polyethylene glycol penetrate the tissue and stabilize the structure. Polyethylene glycol becomes attached, in additionally concentrated form, on the surface of the tissue and protects this tissue from external influences. In addition, the targeted use of polyethylene glycol in combination with glycerol results in a marked reduction of the risk of calcification of the implanted tissue.

According to a particularly preferred embodiment of the invention, the tissue is also exposed—before drying—to another solution, which contains polyethylene glycol having a mean molecular weight, in each case, that differs from that of the previous solution, wherein the tissue is either exposed to the solutions one after the other in any order, or is exposed thereto simultaneously, as a solution mixture. Preferably, the mean molecular weight of the polyethylene glycol of this solution is higher than the mean molecular weight of the polyethylene glycol of the prior solution. In this embodiment of the invention, the solutions can be combined in any manner. This includes the use of three separate solutions, a separate solution and a solution mixture, as well as the use of only one stabilizing solution mixture containing all three solutions. Likewise, in some embodiments, it can be advantageous to use additional solutions that contain polyethylene glycol.

The advantages of the invention are particularly effective in this preferred embodiment. This embodiment is based on the finding made by the inventors that the penetration depth of polyethylene glycol into the biological tissue depends on the molecular weight of the polyethylene glycol itself. Without acquiescing to a specific mechanism of action, it is suspected that this is due to the viscosity changing with the molecular weight. In particular, use of a polyethylene glycol-containing solution having a lower mean molecular weight before a polyethylene glycol-containing solution having a higher mean molecular weight, induces stabilization effects at different tissue depths. In this embodiment of the invention, it is therefore possible, in particular, to retain and stabilize the microscopic tissue structures.

The polyethylene glycol-containing solutions typically contain polyethylene glycol having a mean molecular weight between 150 g/mol and 6000 g/mol. As used herein, the term "between" also includes the upper and lower stated values. As such, a mean molecular weight between 150 g/mol and 6000 g/mol is intended to also include 150 g/mol and 6000 g/mol.

In some embodiments at least one polyethylene glycol-containing solution contains polyethylene glycol having a mean molecular weight between 150 g/mol and 200 g/mol, between 150 g/mol and 300 g/mol, between 200 g/mol and 300 g/mol, between 200 g/mol and 600 g/mol, between 200 g/mol and 400 g/mol, between 150 g/mol and 400 g/mol, or between 400 g/mol and 600 g/mol. According to a particularly preferred embodiment, the polyethylene glycol-containing solution, which is provided before or after a glycerol solution, contains polyethylene glycol at or about 150 g/mol to 300 g/mol or at or about 200 g/mol (e.g. PEG200), and in a still more preferred embodiment, the polyethylene glycol-containing solution contains 40% PEG200 or about 40% PEG200. The term "about" as used herein is intended to encompass a variation above and below the stated amount that would be expected to within ordinary use, such as 5% or 10% variation. Glycerol may be added to any of the above solutions to form a mixture or may be provided separately.

In some embodiments, a subsequently applied polyethylene glycol-containing solution contains polyethylene glycol having a higher mean molecular weight than a prior applied polyethylene glycol-containing solution. In some embodiments, the subsequently applied polyethylene glycol-containing solution contains polyethylene glycol having a mean molecular weight between 200 g/mol and 6000 g/mol. In some embodiments, the subsequently applied polyethylene glycol-containing solution contains polyethylene glycol having a mean molecular weight between 300 g/mol and 1500 g/mol. In some embodiments, the subsequently applied polyethylene glycol-containing solution contains polyethylene glycol having a mean molecular weight between 400 g/mol and 1200 g/mol. In some embodiments, the subsequently applied polyethylene glycol-containing solution contains polyethylene glycol having a mean molecular weight between 400 g/mol and 800 g/mol. In some embodiments the subsequently applied polyethylene glycol-containing solution contains polyethylene glycol having a mean molecular weight between 400 g/mol and 600 g/mol. In some embodiments, the subsequently applied polyethylene glycol-containing solution contains polyethylene glycol having a mean molecular weight of 400 g/mol (PEG400) or about 400 g/mol. Glycerol may be added to any of the above solutions to form a mixture or may be provided separately.

Stabilization can be carried out by sequentially exposing a biological tissue, graft or substrate to a series of stabilizing solutions or can be carried out in part with a solution mixture. In some embodiments, glycerol is provided in a same solution as a polyethylene glycol-containing solution having a mean molecular weight of polyethylene glycol between 150 g/mol and 200 g/mol, between 150 g/mol and 300 g/mol, between 200 g/mol and 300 g/mol, between 200 g/mol and 600 g/mol, between 150 g/mol and 600 g/mol, between 150 g/mol and 400 g/mol, between 200 g/mol and 400 g/mol, between 400 g/mol and 600 g/mol, or 200 g/mol or about 200 g/mol. In some embodiments, after exposing the tissue, graft or substrate to the mixture (preferably after tissue saturation), the tissue, graft or substrate is exposed to a subsequent solution containing polyethylene glycol having a mean molecular weight of polyethylene glycol between 150 g/mol and 6000 g/mol, but preferably at higher mean molecular weight than the mixture. In some embodiments, the subsequently applied polyethylene glycol-containing solution contains polyethylene glycol having a mean molecular weight between 200 g/mol and 6000 g/mol, between 300 g/mol and 1500 g/mol, between 400 g/mol and 1200 g/mol, between 400 g/mol and 800 g/mol, between 400 g/mol and 600 g/mol, or 400 g/mol or about 400 g/mol.

In an alternative embodiment of the invention, the decellularized and/or cross-linked biological tissue is first exposed to a solution containing polyethylene glycol having a mean molecular weight between 150 g/mol and 200 g/mol, between 150 g/mol and 300 g/mol, between 200 g/mol and 300 g/mol, between 200 g/mol and 600 g/mol, between 150 g/mol and 600 g/mol, between 150 g/mol and 400 g/mol, between 200 g/mol and 400 g/mol, between 400 g/mol and 600 g/mol, or 200 g/mol or about 200 g/mol; and, subsequently exposed to a solution containing glycerol or vice versa. Exposure is preferably performed for a time sufficient to saturate the tissue.

In another embodiment of the invention, the biological tissue is first exposed to a solution containing polyethylene glycol having a higher mean molecular weight, such as between 200 g/mol and 6000 g/mol, between 300 g/mol and 1500 g/mol, between 400 g/mol and 1200 g/mol, between 400 g/mol and 800 g/mol, between 400 g/mol and 600 g/mol, or 400 g/mol or about 400 g/mol; and subsequently exposing the biological tissue to a solution containing polyethylene glycol having a lower mean molecular weight, such as between 150 g/mol and 200 g/mol, between 150 g/mol and 300 g/mol, between 200 g/mol and 300 g/mol, between 200 g/mol and 600 g/mol, between 150 g/mol and 600 g/mol, between 150 g/mol and 400 g/mol, between 200 g/mol and 400 g/mol, between 400 g/mol and 600 g/mol, or 200 g/mol or about 200 g/mol; followed by exposing the biological tissue to a solution, which contains glycerol. More preferred would be exposing biological tissue to a solution containing polyethylene glycol having a mean molecular weight of 400 g/mol or about 400 g/mol, and subsequently exposing the biological tissue to a solution containing polyethylene glycol having a mean molecular weight that is lower than the first (e.g. 400 g/mol), such as 150 g/mol to 300 g/mol, 200 g/mol or about 200 g/mol.

In some embodiments the decellularized and/or cross-linked biological tissue is first exposed to a solution containing polyethylene glycol having a mean molecular weight between 150 g/mol and 200 g/mol, between 150 g/mol and 300 g/mol, between 200 g/mol and 300 g/mol, between 200 g/mol and 600 g/mol, between 150 g/mol and 600 g/mol, between 150 g/mol and 400 g/mol, between 200 g/mol and 400 g/mol, between 400 g/mol and 600 g/mol, or 200 g/mol or about 200 g/mol; and, subsequently exposed to a solution containing glycerol and polyethylene glycol having a higher mean molecular weight, such as between 200 g/mol and 6000 g/mol, between 300 g/mol and 1500 g/mol, between 400 g/mol and 1200 g/mol, between 400 g/mol and 800 g/mol, between 400 g/mol and 600 g/mol, or 400 g/mol or about 400 g/mol.

In another embodiment, the biological tissue is first subjected to a treatment with a glycerol-containing solution (e.g. 30% or about 30% glycerol), subsequently to a treatment with a solution containing polyethylene glycol having a low mean molecular weight in the range of 150 g/mol to 300 g/mol, 200 g/mol or about 200 g/mol (e.g. 40% PEG200 or about 40% PEG200), followed by a treatment with a solution, which contains polyethylene glycol having a slightly higher mean molecular weight, such as 400 g/mol or about 400 g/mol (e.g. 40% PEG400 or about 40% PEG400). In this embodiment, it is believed that the glycerol first deeply penetrates the tissue, the lower mean molecular weight polyethylene glycol penetrates the regions of the tissue close to the surface, and the slightly higher molecular weight polyethylene glycol induces sealing of the surface. In this embodiment, the two polyethylene glycol-containing solutions can each independently be from 150 g/mol to 400 g/mol.

Preferably, the tissue is exposed to each of the solutions making up the stabilizing step for a time sufficient to saturate the tissue with either glycerol or polyethylene glycol; however, saturation is not an absolute requirement. As general guidance, exposure to each stabilizing solution for more than about 5 minutes may be sufficient depending on the tissue and conditions. Experimentally it was found that sequentially immersing porcine pericardium tissue in each solution for 15 minutes while shaking at 37° C. was effective. Naturally the exposure time may vary depending on the homogeneity of the tissue, the concentration of saturating agent, whether or not the exposure includes sample mixing, and temperature. Periods longer than 15 minutes have been found effective but not significantly better. As such, the exposure time can vary from 5 minutes to 1 hour, 10 minutes to 30 minutes, 15 or 20 minutes, 5 minutes to 12 hours or more, 1 to 12 hours, 2 to 6 hours, or others.

In any case, polyethylene glycol is advantageously present in each polyethylene glycol containing solution at a concentration of 5 wt % to 70 wt %, preferably of 10 wt % to 60 wt %, most preferably 40 wt % or about 40 wt %. Glycerol is expediently contained in glycerol-containing solution in a concentration of 5% to 65%, preferably 5% to 30%, and most preferably 30% or about 30%. On the one hand, if the amount of stabilizing agent (e.g. glycerol or polyethylene glycol) in the stabilizing solution is too low, the tissue structure will be damaged while drying due to insufficient protection/covering of tissue fibers. On the other hand, a concentration that is too high results in a higher water content of the dried tissue as well as a "greasy" tissue surface.

Within the scope of this application, the unit of measure for the stabilizing solution is "weight %" or "wt %". The unit of measure "weight %" refers to a percentage of weight, within the scope of this application. A 100 g solution having 0.9 weight % of sodium chloride therefore contains 0.9 g sodium chloride.

The artisan will also appreciate that the temperature during the stabilization step may affect results. A temperature that is too high (e.g. above about 85° C.) results in denaturation and irreversible damage of the glutaraldehyde crosslinked tissue. However, a temperature that is too low may result in a solution that is too viscous. Experimentally, exposure to the stabilizing solutions at 37° C. worked well, but temperatures from room temperature up to 60° C. are expected to be fine.

Preferably, the biological tissue is subjected to a pretreatment comprising an optional decellularization with a suitable detergent, preferably a solution containing surfactin and deoxycholic acid, and a subsequent cross-linking, preferably with a glutaraldehyde-containing solution.

The methods described in this application are suitable for the preparation of decellularized tissue, decellularized and cross-linked tissue, or, e.g., decellularized and non-cross-linked tissue. Optionally, all these tissues may be stabilized. Optionally, for all these tissues alpha-galactosidase epitopes have been removed by suitable alpha-galactosidase treatment.

With regard to the device, the stated problem is solved by an implant comprising biological tissue, which is subjected to the method for preparation according to the invention and dried.

In this connection, the drying of the tissue is designed such that a slow and gentle withdrawal of the water, in the liquid state, from the tissue is ensured. This is advantageously achieved by means of the controlled reduction of the ambient humidity of the biological tissue in a desiccator or a climate-controlled chamber under controlled settings of the parameters of the ambient atmosphere of the biological tissue.

The implant is preferably a heart valve prosthesis, which comprises an artificial heart valve made of biological tissue and/or a seal made of biological tissue, which is secured on an expandable or self-expanding support frame, which can be implanted by means of a catheter, preferably the biological tissue being secured on the support frame via suturing.

BRIEF DESCRIPTION OF THE DRAWINGS

FIG. 3 is a table summarizing the amount of free protein measured after decellularization of porcine pericardium with surfactin or surfactin and DCA over time compared to native tissue.

FIG. 6 is a table summarizing the amount of residual DNA measured after decellularization of porcine pericardium with DCA or surfactin and DCA compared to native tissue.

FIG. 10 is a table summarizing the saturation time of porcine pericardium with different stabilizers.

DETAILED DESCRIPTION OF PREFERRED EMBODIMENTS

Figure 1:
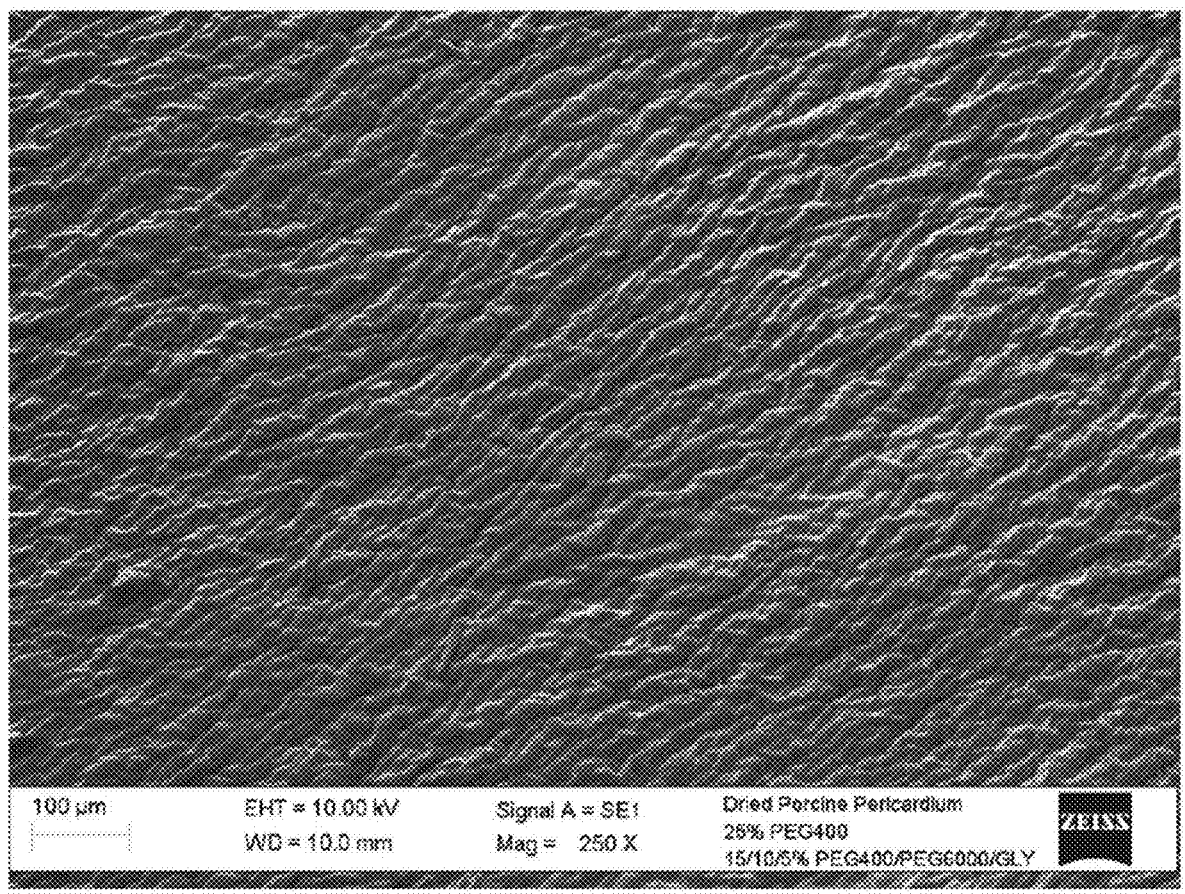
FIG. 1 shows an electron microscopic image of a porcine pericardial tissue according to Example I.
Figure 2:
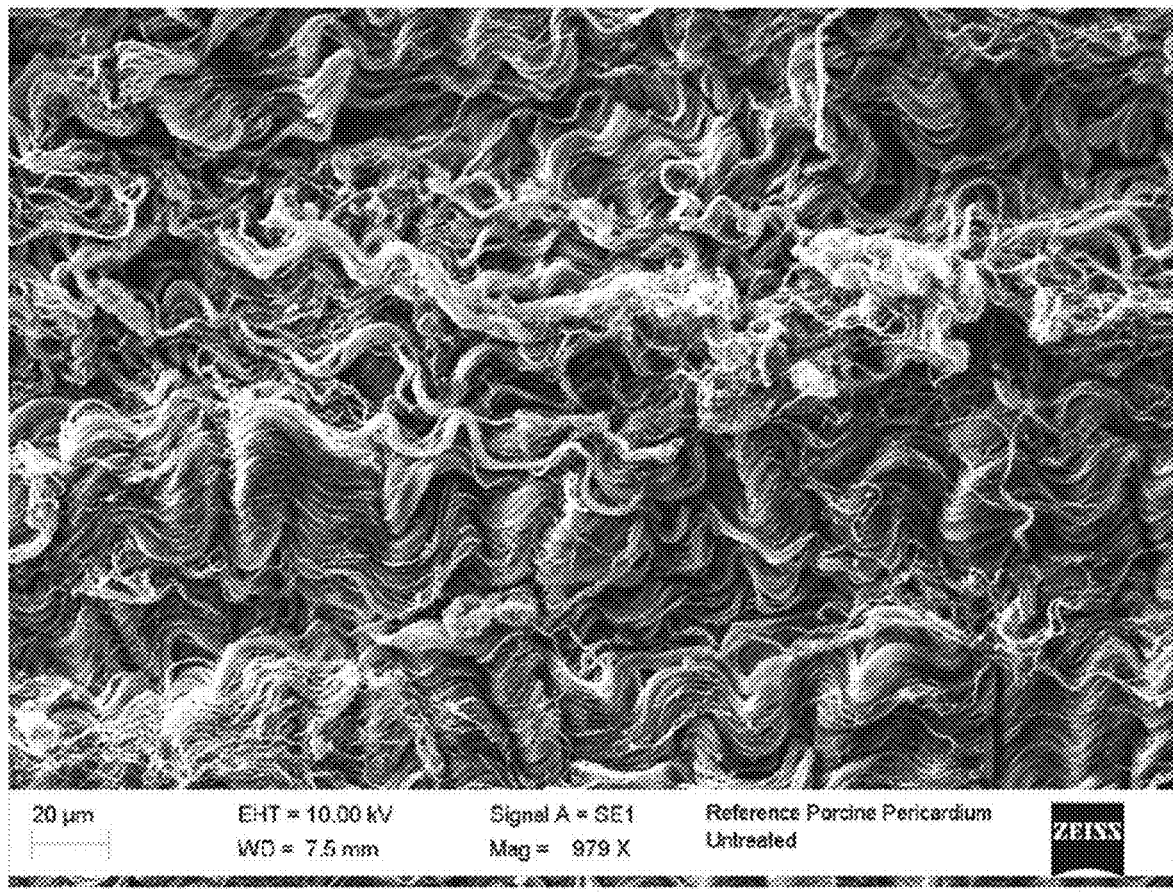
FIG. 2 shows an untreated, cross-linked pericardium, as a reference for comparison to the pericardial tissue shown in FIG. 1.

The invention will be explained in greater detail on the basis of exemplary embodiments and a comparison—depicted in FIGS. 1 and 2—of a dried biological tissue according to one exemplary embodiment of the invention with the prior art.

Example I

Preparation and Drying of Pericardial Tissue

Example I discloses an embodiment of the method according to the invention for the preparation of porcine pericardium with subsequent drying. FIG. 1 shows a porcine pericardial tissue in the dried state after a treatment according to example I. A sealing and stabilization of the surface structure resulting from the treatment with the stabilizers is shown very clearly in the electron microscopic image. The untreated reference tissue shown in FIG. 2 comprises exposed collagen structures, which are present in the unsealed state.

First, a pericardium is removed from a freshly slaughtered pig in a slaughterhouse and is stored in a solution of 0.9 weight % of sodium chloride, which contains penicillin and/or streptomycin, for 2 hours at a temperature of 4° C. In the next step, fat and connective tissue are separated from the pericardial tissue in moist conditions (solution of 0.9 weight % of sodium chloride), and the pericardial tissue is trimmed to the proper size.

Next, the tissue is rinsed (100 ml solution of 0.9 weight % of sodium chloride, accompanied by gentle movement), cross-linked (48 hours in 100 ml solution of 0.6 weight % of glutaraldehyde solution (glutaraldehyde in buffered saline solution at 4-8° C. (DPBS solution from the company Lonza; DPBS w/o Ca++/Mg++; Art. No. 17-512)), wherein this solution then acts for 14 days at room temperature and is replaced with a similar, fresh solution once every 48 hours), and is then rinsed again (rinsed for 10 min in 100 ml solution of 0.9 weight % of sodium chloride at 37° C., accompanied by gentle movement, repeated 6 times).

The thusly treated, cross-linked biological tissue is then subjected to an embodiment of the dimensional and structural stabilization step according to the invention.

In this embodiment, the biological tissue is subjected to a first rinsing for 10 min in 100 ml of an aqueous solution of 25 vol % of polyethylene glycol (containing polyethylene glycol having a mean molecular weight of 400 g/mol at 37° C., repeated 3 times.

Next, the biological tissue is exposed to a second solution mixture for 2 hours at a temperature of 37° C. In this embodiment of the invention, the second solution mixture comprises an aqueous solution containing polyethylene glycol having a mean molecular weight of 400 g/mol in a concentration of 15 vol % of polyethylene glycol having a mean molecular weight of 6000 g/mol in a concentration of 10 vol % and glycerol in a concentration of 5 vol %.

The thusly stabilized biological tissue is then dried in a desiccator for 24 hours, using a silica gel as the desiccant. The thusly obtained, dried, biological tissue can either be further processed or stored in the desiccator.

Within the scope of this application, a desiccator refers to a closed vessel, which contains an active desiccant and has minimal humidity in the interior thereof.

As an alternative, the drying can also take place in a climate-controlled chamber having an adjustable temperature and humidity.

Example II

Preparation and Drying of Pericardial Tissue

Similar to example I, a pericardium is removed from a pig, stored for 2 hours at a temperature of 4° C. in a solution of 0.9 weight % of sodium chloride, which contains penicillin and/or streptomycin, is prepared in moist conditions (solution of 0.9 weight % of sodium chloride) with removal of fat and connective tissue, is trimmed to size, and is subsequently rinsed with 100 ml of a solution of 0.9 weight % of sodium chloride, accompanied by gentle movement.

The thusly obtained pericardium is then subjected to gentle decellularization and subsequent cross-linking. The following steps are carried out:

decellularization in 100 ml surfactin/deoxycholic acid solution (0.06 weight % of surfactin and 0.5 weight % of deoxycholic acid in a solution of 0.9 weight % of sodium chloride) for 20 hours at 37° C., rinsing with 100 ml of a solution of 0.9 weight % of sodium chloride (6 times, accompanied by gentle movement, for 10 min)

treatment with a DNase solution for 12 hours at 37° C.

rinsing with 100 ml of a solution of 0.9 weight % of sodium chloride (8 times, accompanied by gentle movement, for 10 min)

rinsing with 100 ml of a solution of 70 vol % of ethanol (once, for 10 min)

rinsing with 100 ml of a solution of 0.9 weight % of sodium chloride cross-linking with glutaraldehyde (48 hours in 100 ml of a solution of 0.6 weight % of glutaraldehyde (glutaraldehyde in buffered saline solution at 4-8° C. (DPBS solution from the company Lonza; DPBS w/o Ca++/Mg++; Art. No. 17-512)), wherein this solution then acts for 14 days at room temperature and is replaced with a similar, fresh solution once every 48 hours)

rinsing with 100 ml of a solution of 0.9 weight % of sodium chloride (6 times, accompanied by gentle movement, for 10 min)

In this embodiment of the invention, the thusly produced, decellularized and cross-linked pericardial tissue is stabilized in three steps. First, the tissue is rinsed with 100 ml of an aqueous solution of 25 vol % of polyethylene glycol (containing polyethylene glycol having a mean molecular weight of 400 g/mol at 37° C., 3 times for 10 min). Next, the tissue is exposed to an aqueous solution containing 20 vol % of polyethylene glycol having a mean molecular weight of 400 g/mol and 10 vol % of glycerol for 2 hours at 37° C., accompanied by gentle movement. This is followed by a treatment with an aqueous solution containing 20 vol % of polyethylene glycol having a mean molecular weight of 6000 g/mol and 10 vol % of glycerol, accompanied by gentle movement, at a constant temperature for 2 hours.

The thusly stabilized biological tissue is then dried in a desiccator for 24 hours, using a silica gel as the desiccant, and is then further processed.

Example III

Stabilization and Drying of Cross-Linked Pericardial Tissue

In the embodiment according to example III, already cross-linked porcine pericardial tissue is prepared (stabilized and dried) using the following method:
- rinsing with 100 ml of a solution of 0.9 weight % of sodium chloride (6 times, accompanied by gentle movement, for 10 min, at room temperature),
- rinsing with 100 ml of an aqueous solution of 40 vol % of glycerol (3 times, accompanied by gentle movement, for 20 min at 37° C.),
- placing the pericardial tissue in an aqueous solution containing 30 vol % of polyethylene glycol having a mean molecular weight of 400 g/mol and 10 vol % of glycerol for 2 hours at 37° C., accompanied by gentle movement,
- placing the pericardial tissue in an aqueous solution containing 30 vol % of polyethylene glycol having a mean molecular weight of 6000 g/mol and 10 vol % of glycerol for 2 hours at 37° C., accompanied by gentle movement, and
- drying in the desiccator for 24 hours, using silica gel as the desiccant.

Example IV

Decellularization of Pericardial Tissue Using a Mixture of Surfactin and DCA as Decellularizing Agent Significantly Reduces Residual Free Protein Free proteins in biological tissue are mostly intracellular proteins that are released when the cell membrane is destroyed. In contrast to the fibrous proteins in the extracellular matrix, free proteins can be extracted and quantified in solution after an extraction. The lower the amount of free proteins in the extraction solution, the better the quality of the decellularization.

For analysis, punched (circle diameter 16 mm) and then freeze-dried tissue samples of porcine pericardium are placed in individual 2 ml reaction vessels for extraction. The dry mass is first determined on a precision balance. Extraction is performed in 1.2 ml DPBS (Dulbeccos phosphate buffered saline solution without Ca/Mg) at 37° C. for 72 hours under continuous agitation. After extraction, the samples are centrifuged at 13000 rpm for five minutes. The sample to be measured with the free proteins is taken from the upper part of the extraction solution.

The amount of free protein before/after decellularization was measured by fluorescence labeling with the "Qubit protein assay kit" in the fluorometer "Qubit 2.0" (both from Invitrogen) according to the standard instructions. The amount of free proteins is related to the sample mass according to the following formula:

Free proteins ($\mu$g/mg)=measured concentration ($\mu$g/ml)×extraction volume (ml)/sample mass (mg)

Figure 4:
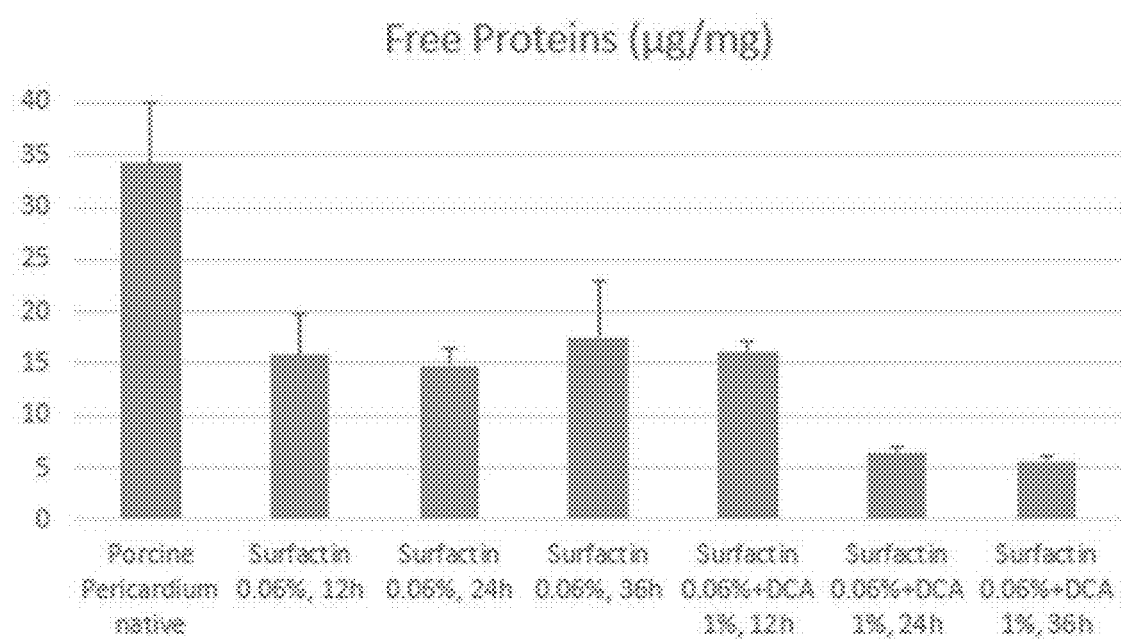
FIG. 4 is a graphical depiction of the amount of free protein after decellularization of porcine pericardium with surfactin or surfactin and DCA over time compared to native tissue.
Figure 5:
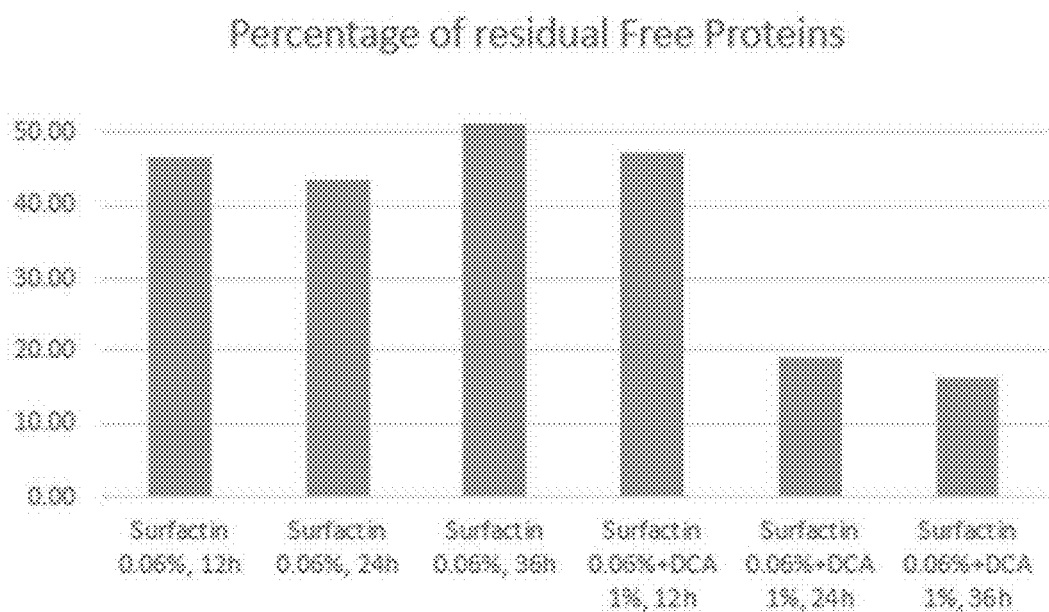
FIG. 5 is a graphical depiction of the amount of residual free protein after decellularization of porcine pericardium with surfactin or surfactin and DCA over time compared to native tissue.

In order to investigate the influence of the combination of surfactin and deoxycholic acid on decellularization, porcine pericardium was examined on the amount of remaining free proteins in its native state as a reference and after decellularization in only 0.06% surfactin and the mixture of 0.06% surfactin and 1% deoxycholic acid (DCA). The surfactin concentration of 0.06% is lower than the solubility in water and higher than the critical micelle formation concentration, whereby the surface tension remains constant during decellularization. The results are shown in FIGS. 3-5.

The measured values with only surfactin 0.06% show no big differences for the different times. However, they scatter more strongly at the shortest exposure time, which indicates inconsistent decellularization. With only 0.06% surfactin, on average only 55% of the soluble proteins are removed compared to native tissue.

This can be significantly improved by using the combination surfactin 0.06%/DCA 1%, whereby more free proteins are removed with increasing decellularization time. After decellularization for 12 hours, about 47.10% of the free proteins remain in the tissue. After 24 hours, this value is reduced to 19.09%, and after 36 hours, to 16.43%. Thus, additional 28.10% of the free proteins are removed from the tissue during decellularization over 24 hours compared to 12 hours. In contrast, the value decreases by only 2.66% during further 12 hours.

The mixture of surfactin and deoxycholic acid therefore allows effective decellularization of porcine pericardium within 24 hours.

Example V

Decellularization of Pericardial Tissue Using a Mixture of Surfactin and DCA as Decellularizing Agent Significantly Reduces Residual DNA Animal DNA in biological tissue used as implant material activates the immune system. This reaction promotes the tendency of porcine pericardium to calcify, contributing to the limited long-term stability of biological valve replacement materials. The reduction of residual DNA in animal tissue is therefore also a goal of decellularization. The smaller the amount of residual DNA the better the quality of decellularization.

For analysis, punched (circle diameter 16 mm) and then freeze-dried tissue samples of porcine pericardium are placed in individual 2 ml reaction vessels. The dry mass is first determined on a precision balance. To determine the residual DNA, the samples are dissolved enzymatically using the enzyme Proteinase K (60° C. in 1000 $\mu$l TRIS reaction buffer at pH 8 with 40 $\mu$l enzyme solution). After complete dissolution of the tissue, the samples are centrifuged at 13000 rpm for five minutes. The sample with the residual DNA to be measured is taken from the upper part of the solution.

The amount of residual DNA before/after decellularization was measured by fluorescence labeling with the "Qubit dsDNA HS kit" in the fluorometer "Qubit 2.0" (both from Invitrogen) according to the standard instructions. The amount of residual DNA is related to the sample mass according to the following formula:

Residual DNA (ng/ml)=measured value (ng/ml)×200 $\mu$l/sample volume ($\mu$l)×1040 $\mu$l/sample mass (mg)

Figure 7:
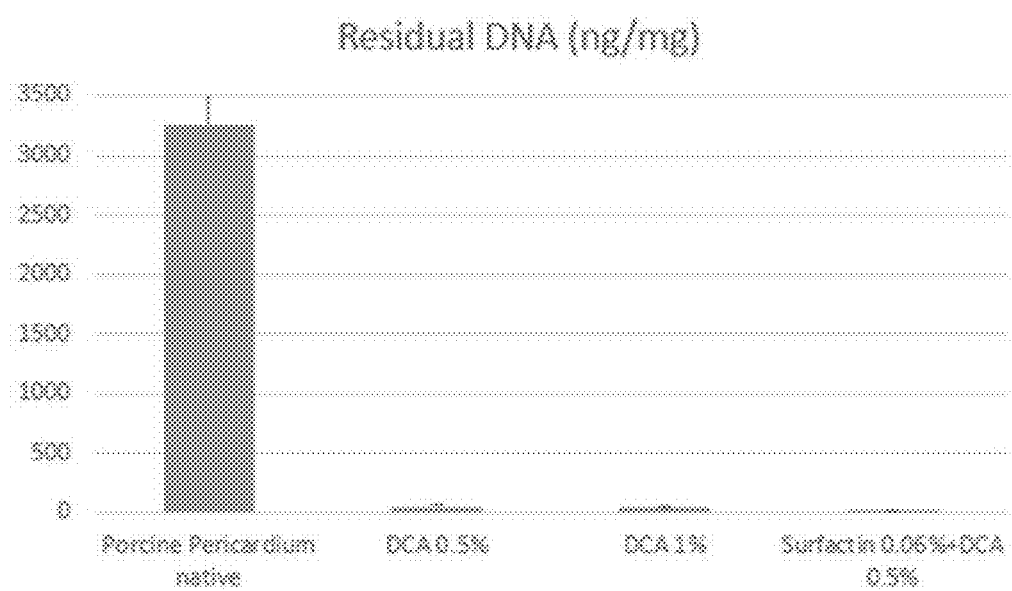
FIG. 7 is a graphical depiction of the amount of residual DNA after decellularization of porcine pericardium with DCA or surfactin and DCA compared to native tissue.
Figure 8:
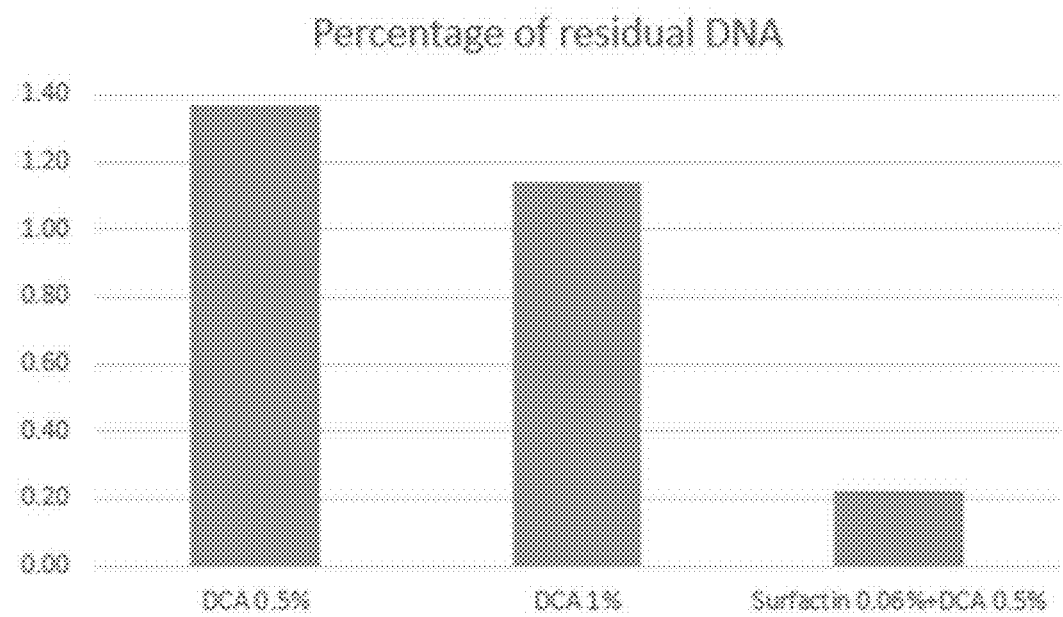
FIG. 8 is a graphical depiction of the percentage of residual DNA after decellularization of porcine pericardium with DCA or surfactin and DCA compared to native tissue.

In order to investigate the influence of the combination of surfactin and deoxycholic acid on decellularization, porcine pericardium was examined on the amount of residual DNA in its native state as a reference and after 24 hours decellularization in only 0.5% and 1% deoxycholic acid (DCA), respectively, as well as the mixture of 0.06% surfactin and 0.5% deoxycholic acid. The surfactin concentration of 0.06% is smaller than the solubility in water and larger than the critical micelle formation concentration, whereby the surface tension remains constant during decellularization. The results are shown in FIGS. 6-8.

The measured values with only deoxycholic acid show a reduction of the residual DNA compared to native tissue for both concentrations 0.5% and 1%. The reduction is greater at the higher concentration.

By using the combination Surfactin 0.06%/DCA 0.5%, the residual DNA content can be further reduced by a factor of five compared to DCA 1%. After decellularization for 24 hours, the residual DNA content is only 0.22%. This is significantly lower than the amount of residual DNA when using deoxycholic acid alone.

The mixture of surfactin and deoxycholic acid therefore allows effective decellularization of porcine pericardium within 24 hours.

Given the exemplary results of the above example portion, the inventors unexpectedly found that a combination of surfactin and DCA for decellularization has a significant advantage over the use of surfactin or DCA alone. In particular, when decellularizing only with surfactin, more soluble proteins remain in the tissue than with a combination with DCA. When decellularizing only with DCA, more residual DNA remains in the tissue than in combination with surfactin. It has been thus surprisingly found that decellularization of biological tissue with a combination of surfactin and DCA permits particularly thorough removal of all these undesired remaining tissue components. Experimentally, it has been shown that a combination of surfactin and DCA produces a particularly good decellularizing agent which is better at removing unwanted tissue components than either agent alone.

Example VI

Stabilization of Biological Tissue with Glycerol and Polyethylene Glycol

In order to stabilize the dimension and structure of biological tissue, the tissue is exposed to several solutions containing glycerol and polyethylene glycol (PEG). Measurements of the actual saturation time for different solutions were accomplished using Fourier transformed infrared spectroscopy (FTIR) combined with an attenuated total reflection (ATR) cell. Since only the tissue surface is considered in the measurement set-up, the saturation of the pericardial tissue over time can be obtained.

Fourier transform infrared (FTIR) spectra were recorded using a Jasco FT/IR-460 Plus spectrometer equipped with a liquid nitrogen cooled solid-state detector (mercury cadmium telluride; MCT) and an attenuated total reflection (ATR) sampling accessory (MIRacle ATR, PIKE Tech). For $CO_2$ correction the spectrometer was purged with a constant flow of nitrogen (0.1 bar). FTIR spectra were acquired from (4000-700) $cm^{-1}$ with 2 $cm^{-1}$ spectral resolution.

Pericardial tissue was harvested, cleaned and cross-linked with glutaraldehyde. The glutaraldehyde cross-linked pericardial tissue was rinsed (2×10 min with saline solution; 1×5 min with purified water) and die-cut in samples circular in size with an 8 mm diameter. Excess water was removed by dipping on a filter paper (Sartorius, FT-3-208-090). Tissue samples were placed with rough side down on the bottom of a cylindrical plastic tube (6 mm diameter, 14 mm height), mounted through press fitting with a slightly wider cylindrical plastic tube and placed on the ATR-diamond (rough side facing the ATR-diamond). 50 µL of glycerol (30% (aqueous solution); 100%), respectively PEG (40% (aqueous solution); 100%), solution was added on top of the tissue sample in the tube. To ensure the maximum contact area between tissue and diamond the tube was fixated with the pressure arm of the spectrometer. FTIR spectra were recorded every 2 min during 1 h. For glycerol the 1140-950 $cm^{-1}$ region was identified as suitable for peak analysis as well as the 1170-970 $cm^{-1}$ region for PEG.

The intensity of the absorption band increases with the saturation of the pericardial tissue. Thus, the peak area was determined and plotted as a function of the incubation time, whereas a normalization was done towards the last ten measurement values (total measurement time: 1 h) assuming that a saturation is reached. The progress of saturation was fitted with a 4-parameter-logistic-function using the Levenberg-Marquardt-Algorithm. The time of saturation (95%) is determined according to Equation 1, the deviation was calculated through error propagation as shown in Equation 2

$$t(y) = x_0 \left( \frac{A_1 - A_2}{y - A_2} - 1 \right)^{1/p} \qquad \text{Equation (1)}$$

Where: $A_1$: lower asymptote
$A_2$ upper asymptote
$x_0$: point of inflection
p: slope at the point of inflection
y: normalized measurement data $$\Delta t(y) = \frac{\partial t(y)}{\partial y} \Delta y \qquad \text{Equation (2)}$$

Figure 9A:
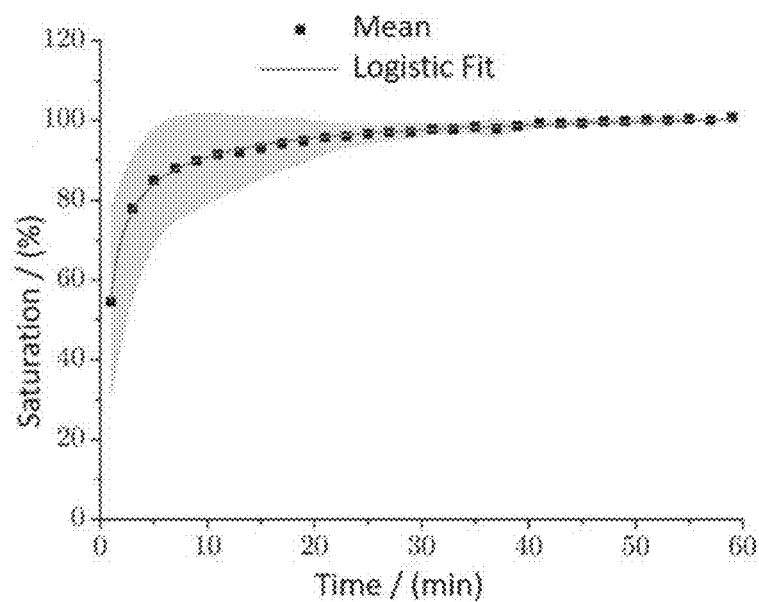
FIGS. 9A-C are graphical depictions of the saturation of glutaraldehyde crosslinked porcine pericardium with 30% glycerol (FIG. 9A), 40% PEG200 (FIG. 9B), and 40% PEG400 (FIG. 9C).
Figure 9B:
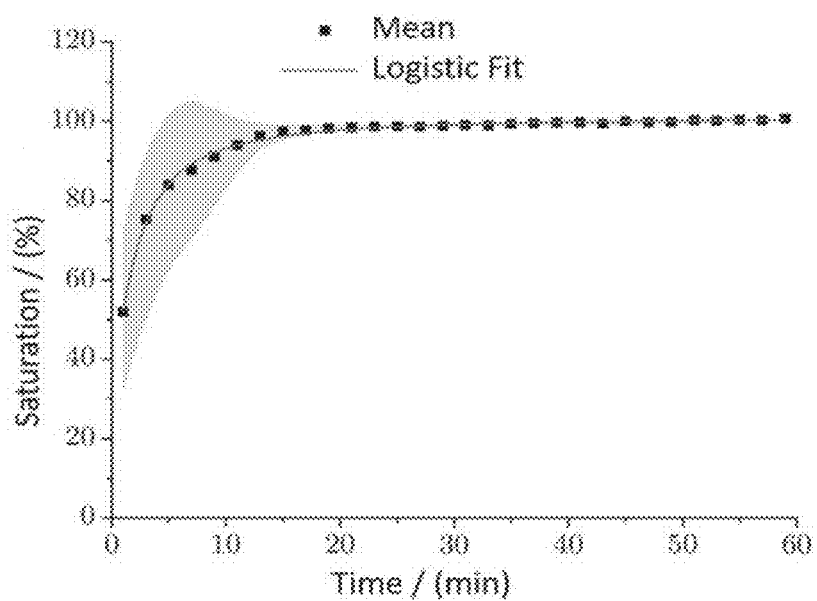
Figure 9C:
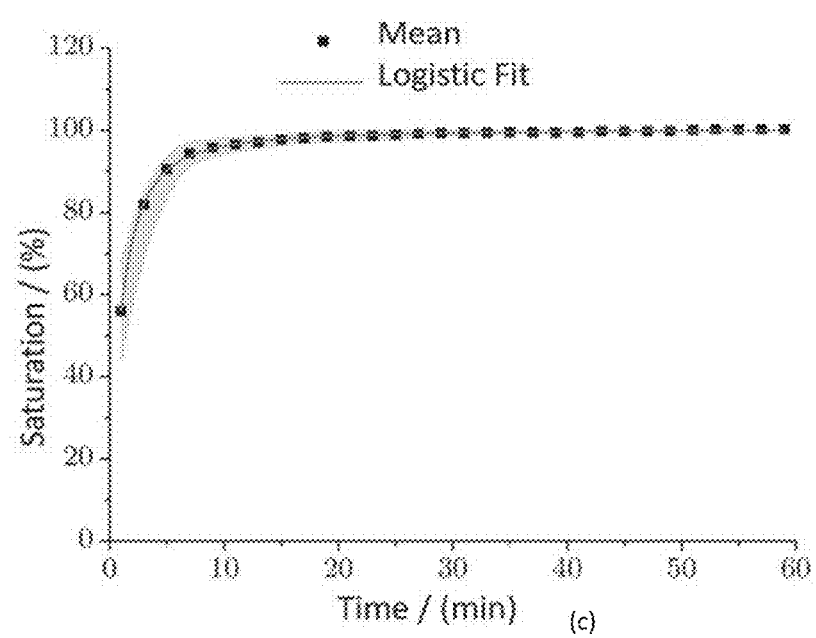

Saturation as a function of incubation time is shown exemplary for glutaraldehyde cross-linked porcine pericardium in FIGS. 9-A-C, and the results for the saturation time are represented in FIG. 10. Exposure occurred at 37° C. while shaking.

Experimentally, it was found that tissue saturation using stabilizing solutions containing glycerol and polyethylene glycol requires far less than 1 hour.

What is claimed is:

1. A method of preparing biological tissue for use as a component of an implant, the method comprising decellularizing biological tissue with a detergent comprising surfactin and deoxycholic acid (DCA).

2. The method according to claim 1, wherein the method is a method of preparing biological tissue for use as a vascular implant.

3. The method according to claim 1, wherein the detergent comprises about 0.06% surfactin.

4. The method according to claim 1, wherein the method is a method of preparing biological tissue for use as a heart valve prosthesis.

5. The method according to claim 1, wherein the detergent comprises about 0.5% DCA.

6. The method according to claim 5, wherein the detergent comprises about 0.06% surfactin.

7. The method according to claim 1, the method further comprising cross-linking the decellularized biological tissue with a cross-linking agent.

8. The method according to claim 7, wherein the cross-linking agent is an aldehyde-containing solution.

9. The method according to claim 7, the method further comprising performing a structural stabilization step on the decellularized tissue before or after cross-linking.

10. The method according to claim 9, wherein the structure stabilization step is performed on the decellularized tissue after cross-linking.

11. The method according to claim 9, wherein the structure stabilization step comprises exposing the decellularized tissue to at least two different solutions, wherein one solution comprises polyethylene glycol and another solution comprises glycerol.

12. The method according to claim 8, wherein the cross-linking agent is a glutaraldehyde or a formaldehyde containing solution.

13. The method according to claim 8, wherein the cross-linking agent is glutaraldehyde.

14. The method according to claim 11, further comprising drying the tissue in a climate chamber by reducing relative humidity.

15. The method according to claim 11, further comprising drying the tissue in a climate chamber by reducing relative humidity from 95% to 10% over 12 hours at 37° C.

16. The method according to claim 11, wherein of the at least two different solutions, a first solution comprises polyethylene glycol having a mean molecular weight between 200 g/mol and 600 g/mol; and a second solution is an aqueous solution of polyethylene glycol having a mean molecular weight between 200 g/mol and 6,000 g/mol and glycerol.

17. The method according to claim 11, wherein the at least two different solutions comprise three different solutions.

18. The method according to claim 17, wherein the first solution comprises glycerol, the second solution comprises polyethylene glycol having a mean molecular weight of or about 200 g/mol and the third solution comprises polyethylene glycol having a mean molecular weight of or about 400 g/mol, wherein the tissue is exposed to the first and second solutions before the third solution, and wherein the mean molecular weight of the polyethylene glycol is higher in the third solution than the second.

19. The method according to claim 1, the method further comprising performing a structural stabilization step on the decellularized tissue.

20. The method according to claim 1, further comprising exposing the decellularized tissue to at least two different solutions, wherein one solution comprises polyethylene glycol and another solution comprises glycerol.

21. The method according to claim 20, further comprising drying the tissue in a climate chamber by reducing relative humidity.

22. The method according to claim 20, further comprising drying the tissue in a climate chamber by reducing relative humidity from 95% to 10% over 12 hours at 37° C.

23. The method according to claim 20, wherein a first solution comprises polyethylene glycol having a mean molecular weight between 200 g/mol and 400 g/mol.

24. The method according to claim 20, wherein the at least two different solutions comprise three different solutions.

25. The method according to claim 24, wherein the polyethylene glycol in the third solution has a mean molecular weight of 300 to 1500 g/mol.

* * * * *